United States Patent [19]

Brunner

[11] Patent Number: 5,989,201

[45] Date of Patent: Nov. 23, 1999

[54] DEVICE FOR MEASURING THE MOBILITY OF THE BACK OR TRUNK OF A PATIENT

[75] Inventor: Wolfgang Brunner, Isny Deutchland, Germany

[73] Assignee: Zebris Medizintechnik Gmbh, Isny, Germany

[21] Appl. No.: 08/979,953

[22] Filed: Nov. 26, 1997

[30] Foreign Application Priority Data

Nov. 28, 1996 [DE] Germany ............................ 196 49 399

[51] Int. Cl.$^6$ ..................................................... A61B 5/00
[52] U.S. Cl. ............................................................. 600/595
[58] Field of Search .................................... 600/587, 594, 600/595

[56] References Cited

U.S. PATENT DOCUMENTS

| | | | |
|---|---|---|---|
| 4,699,156 | 10/1987 | Gracovetsky | 600/595 |
| 5,143,088 | 9/1992 | Marras et al. | 600/594 |
| 5,203,346 | 4/1993 | Fuhr et al. | 600/594 |
| 5,337,758 | 8/1994 | Moore et al. | 600/595 |
| 5,398,697 | 3/1995 | Spielman | 600/595 |

*Primary Examiner*—Max Hindenburg
*Attorney, Agent, or Firm*—Antonelli, Terry, Stout & Kraus, LLP

[57] ABSTRACT

The invention relates to a device for measuring the mobility of the back or trunk of a patient by determining the travel of the three-dimensional absolute positions of at least three reference points in a reference area of the device with respect to a stationary measuring device with a contact area forming a support plane, with the reference points defining a reference area that is located transversely with respect to the support plane.

7 Claims, 1 Drawing Sheet

DEVICE FOR MEASURING THE MOBILITY OF THE BACK OR TRUNK OF A PATIENT

BACKGROUND OF THE INVENTION

The invention relates to a device for measuring the mobility of the back or trunk of a patient by determining the travel of the three-dimensional absolute positions of at least three reference points in a reference area of the device relative to a stationary measuring device with a contact area forming a support plane.

It is known that the mobility of the trunk and/or back of a patient can be determined by gluing marking points on the back as reference points ("Study of Gait and Functional Spinal Column Measurement by Means of a Newly-Developed Real-Time Stereo Ultrasound Topometer (ESUT)," in Functional Diagnosis in Orthopedics, Enkeverlag, Stuttgart, 1979). Determination of the mobility of the back and trunk can provide valuable information.

In order to determine the absolute position of all the degrees of freedom of a specific part of the trunk, at least three differential points must be located per area of the trunk. The reference points can consist for example of ultrasonic transmitters or receivers whose position can be determined by a stationary measuring station, stationary measuring microphones or sonic transmitters for example, through measurements of running time (EP-0 305 780).

Other methods include the location of reflecting or light-emitting reference points by means of correspondingly stationary recording cameras with evaluation connected to them as a stationary measuring device.

In these known devices, it is disadvantageous that in severe forward tilting of the subject, the stationary measuring device can no longer be located, or can no longer be located accurately, because the body then comes between the area between the reference points and the stationary measuring device.

SUMMARY OF THE INVENTION

Hence the goal of the invention is to improve a device for measuring the mobility of the back or trunk of a patient in such fashion that the reference points can be located with all degrees of freedom of movement, especially in severe forward tilting of the subject away from the stationary measuring device.

The device is attached immovably to the body of the subject, using a belt for example. Because of the transverse arrangement of the reference points defining the reference surface relative to the support plane, the device can be attached in such fashion that the reference surface lies in the sagittal plane. This permits a constant sight-free contact between the reference points and the stationary measuring device without there being a risk that if the subject tilts his body forward by a certain amount, his back, head, or trunk will cover this area, making measurement impossible, more difficult, or distorted. In particular, a new-radiation position of the subject in a certain aligned position can be defined. Since the reference points have visual contact with the stationary measuring device at all times and as a rule have only a limited receiving and/or radiating lobe, by virtue of the device according to the invention, with the degrees of freedom for tilting forward and backward, tilting sideways, and rotation, constant direct contact and/or visual contact of all the reference points with respect to the stationary measuring device is ensured.

At the same time, by means of a lockable joint, alignment of the reference points can be performed when the subject is standing upright, which is necessary in order to be able to distinguish between certain directions of motion, tilting forward or backward for example.

Advantageous embodiments and improvements on the invention are characterized in the subclaims.

One embodiment of the invention will now be explained below with reference to FIGS. 1 and 2.

DETAILED DESCRIPTION OF THE PREFERRED EMBODIMENTS

Figure 1:
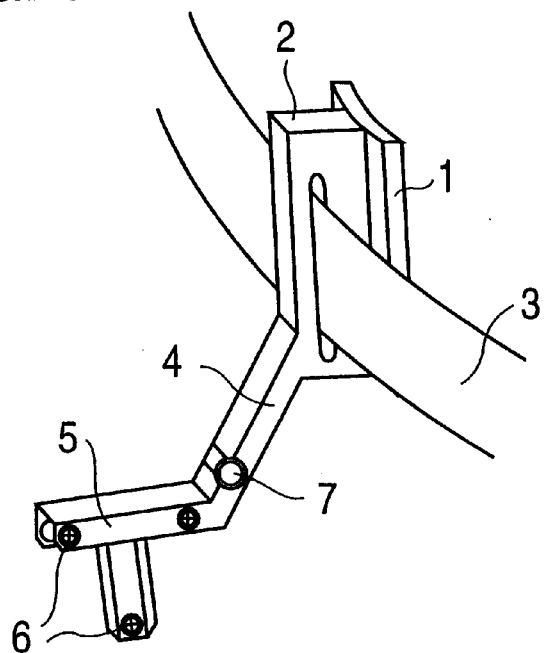
FIG. 1 shows the device in a schematic side view.

The contact area that forms a support plane 1 is provided at the back with a spacer 2. The latter is equipped with a slot for a belt 3 to pass through, said belt, placed around the body of the subject, securing the device immovably to him. This spacer 2 is connected to a holder 4 with reference area 5 located at its end as a support for reference points 6 by means of a lockable joint 7.

Figure 2:
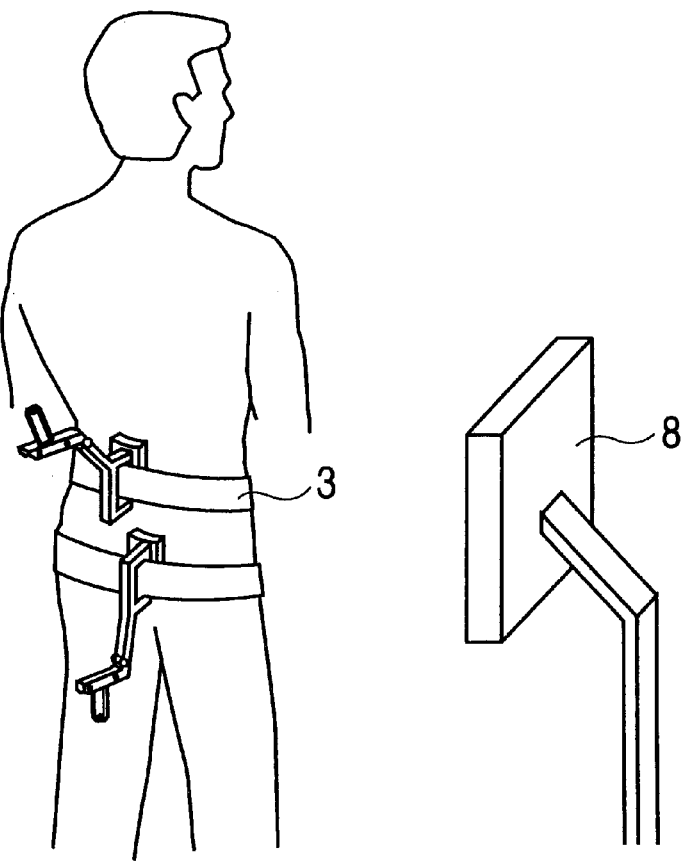
FIG. 2 shows two devices mounted on a subject according to FIG. 1 in a schematic perspective view.

With a suitable arrangement of two such devices with belt 3 on the back of a subject (FIG. 2), firstly the two reference areas can be placed on the sides of the two devices that face away from one another in order to prevent these devices striking one another during movement. In addition, the reference surface formed by reference points 6 can be adjusted in the sagittal plane of the subject, in any case transversely and preferably perpendicularly to the support plane. This results in a constant visual contact between stationary measuring device 8 and individual reference points 6.

The evaluation of the signals emitted by the reference points (sound-light) is performed in a manner known of itself.

I claim:

1. Device for measuring the mobility of the back or trunk of a patient by determining the travel of the three-dimensional absolute positions of at least three reference points in a reference area of the device with respect to a stationary measuring device, with a contact area forming a support plane, characterized in that reference points define a reference area that extends at a right angle to the support plane, the contact area being provided with a spacer for a belt adapted to be placed around the body of the patient, the contact area and/or the spacer being connected with the reference area by a holder.

2. Device according to claim 1, characterized in that the angle of inclination of the holder relative to the reference area is designed to be adjustable, preferably in the sagittal plane.

3. Device according to claim 2 characterized in that the angle of inclination of holder relative to the reference area can be adjusted by means of a lockable joint.

4. Device according to claim 1, characterized in that reference points are designed as small ultrasonic transmitters or receivers that are located by measuring the travel time to stationary measuring device using sonic receivers or transmitters.

5. Device according to claim 1, characterized in that reference points is designed as passive reflectors or as active labeling points in the form of light transmitters that can be located by a camera as a stationary measuring device and corresponding evaluation devices.

6. Device according to claim 1, characterized in that the stationary device for determining the position of reference points can be located essentially laterally with respect to the subject.

7. Device according to claim 1, characterized in that the holder extends at an angle to the reference area along one of the two sides of belt in the sagittal plane.

* * * * *